United States Patent
Barnes et al.

(10) Patent No.: US 10,630,814 B2
(45) Date of Patent: Apr. 21, 2020

(54) SERIAL INTERFACE TO TRANSMISSION CONTROL PROTOCOL INTERFACE MULTI-PORT COMMUNICATION DEVICE

(71) Applicant: CERNER INNOVATION, INC., Kansas City, KS (US)

(72) Inventors: Michael Thomas Barnes, Overland Park, KS (US); Raymond B. Smith, Olathe, KS (US); Dharmesh Jagadish, Kansas City, MO (US); John Harold Volkens, Overland Park, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 163 days.

(21) Appl. No.: 15/689,732

(22) Filed: Aug. 29, 2017

(65) Prior Publication Data

US 2019/0068760 A1 Feb. 28, 2019

(51) Int. Cl.
*H04L 29/06* (2006.01)
*H04L 29/08* (2006.01)
*G06Q 50/22* (2018.01)

(52) U.S. Cl.
CPC .......... *H04L 69/163* (2013.01); *G06Q 50/22* (2013.01); *H04L 67/04* (2013.01); *H04L 67/1093* (2013.01); *H04L 67/125* (2013.01)

(58) Field of Classification Search
CPC ... H04L 69/163; H04L 67/04; H04L 67/1093; G06Q 50/22
See application file for complete search history.

(56) References Cited

U.S. PATENT DOCUMENTS

| | | | |
|---|---|---|---|
| 2002/0075297 A1* | 6/2002 | Boulter | G06F 3/14 715/736 |
| 2004/0176667 A1* | 9/2004 | Mihai | A61B 5/0002 600/300 |
| 2006/0064324 A1* | 3/2006 | Rosenfeld | G16H 50/20 705/2 |
| 2008/0097908 A1* | 4/2008 | Dicks | A61B 5/0022 705/50 |
| 2010/0169120 A1 | 7/2010 | Herbst et al. | |
| 2011/0001605 A1* | 1/2011 | Kiani | G06F 19/3418 340/5.6 |
| 2017/0053086 A1* | 2/2017 | Martin | G06F 19/3418 |

* cited by examiner

*Primary Examiner* — Albert T Chou
(74) *Attorney, Agent, or Firm* — Shook, Hardy & Bacon LLP

(57) ABSTRACT

A multi-port communication device having a plurality of serial interfaces and a plurality of Transmission Control Protocol (TCP) interfaces is provided. Data is received from one or more medical devices at a serial interface of the plurality of serial interfaces and communicated to a healthcare information system via a TCP interface of the plurality of TCP interfaces. The multi-port communication device can be remotely managed by a remote device via a set of management tools. In embodiments, the set of management tools run locally on the multi-port communication device. The multi-port communication device may additionally comprise locally installed drivers that enable communication with the healthcare information system via TCP.

19 Claims, 7 Drawing Sheets

SERIAL INTERFACE TO TRANSMISSION CONTROL PROTOCOL INTERFACE MULTI-PORT COMMUNICATION DEVICE

BACKGROUND

Terminal servers are traditionally used in a heath care setting by connectivity servers (e.g., CareAware® iBus) to facilitate MDI (e.g., laboratory devices) connectivity to a healthcare information system (which may include an EMR). Typically, medical devices (e.g., laboratory devices) utilize serial interface ports to connect to the terminal servers. The terminal servers are disparate systems that provide raw network socket connections to serial interfaces on the medical devices. Upon connecting the medical devices, terminal servers utilize TCP interface ports to provide basic serial to TCP conversion capability and facilitate communication from the medical devices to the healthcare information system. However, current terminal servers are utilized with unauthenticated TCP port access with no restrictions on what addresses can access each port. Human error or malicious intent can result in multiple foreign systems trying to access the same TCP port, which results in missing or spotty data.

Hardware can be difficult to obtain and many of the terminal server designs have had no significant updates to the hardware or software. Many terminal servers in production today have a single 10BaseT Ethernet. The 10 MHz speed translates to 10 Mbit per second, which in theory means 1.2 Mbps. In practice though, the current terminal server is limited to no more than 800 kilobits per second (Kbps) because the 10BasetT Ethernet runs at half-duplex. Although that is sufficient bandwidth for serial devices running at 9600 bits per second, the half-duplex nature along with the limited processing power, makes these terminal servers susceptible to denial of service (intentional or unintentional), especially if network designs are not taking into consideration this risk.

However, terminal servers are very simple devices that require a signification amount of manual configuration, often using proprietary software or non-intuitive command line interfaces to configure, receive status updates, and reset serial port connections. Moreover, the TCP interface ports are not managed which can result in a loss of connectivity, which is not easily recognized until a clinician searches the EMR and realizes the data is missing. Even when it is determined that a loss of connectivity has occurred, clinicians are not equipped to troubleshoot the terminal server via proprietary software or command line utilities. Accordingly, support requests must be generated and routed through a support system until someone properly trained to troubleshoot the terminal server is available and on-site. This level of support results in numerous support requests for changes and simple management tasks which increases costs and time delays to support and manage the terminal servers.

Issues related to terminal servers have led to an implementation shift. In an effort to minimize network related impacts on the reliability of the terminal server, more hardware has been placed closer to the terminal server. For example, a CE appliance or a SOAD server are sometimes utilized to servers to connect the terminal servers to a bus that supports the healthcare information system. Although the additional hardware has helped to reduce some of the support related issues, the hardware costs have significantly increased.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention generally relate to a multi-port communication device. More particularly, embodiments of the present invention relate to a multi-port communication device having a plurality of serial interfaces and a plurality of Transmission Control Protocol (TCP) interfaces. Data is received from one or more medical devices at a serial interface of the plurality of serial interfaces and communicated to a healthcare information system via a TCP interface of the plurality of TCP interfaces. The multi-port communication device can be remotely managed by a remote device via a set of management tools. In embodiments, the set of management tools run locally on the multi-port communication device. The multi-port communication device may additionally comprise locally installed drivers that enable communication with the healthcare information system via TCP.

BRIEF DESCRIPTION OF THE DRAWINGS

Embodiments are described in detail below with reference to the attached drawing figures, wherein.

DETAILED DESCRIPTION

Figure 1:
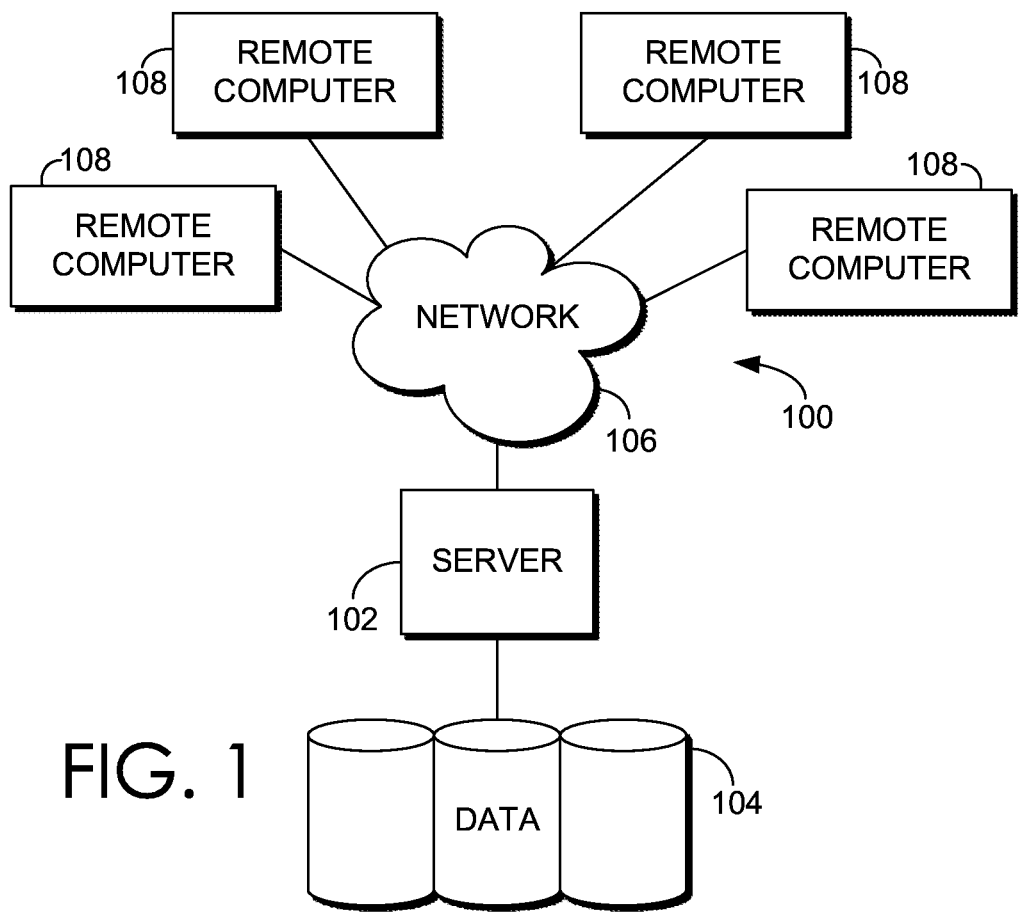
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

As noted in the Background, terminal servers are traditionally used in a heath care setting by connectivity servers (e.g., CareAware® iBus) to facilitate MDI (e.g., laboratory devices) connectivity to a healthcare information system (which may include an EMR). Typically, medical devices (e.g., laboratory devices) utilize serial interface ports to connect to the terminal servers. The terminal servers are disparate systems that provide raw network socket connections to serial interfaces on the medical devices. Upon connecting the medical devices, terminal servers utilize TCP interface ports to provide basic serial to TCP conversion capability and facilitate communication from the medical devices to the healthcare information system. However, current terminal servers are utilized with unauthenticated TCP port access with no restrictions on what addresses can access each port. Human error or malicious intent can result in multiple foreign systems trying to access the same TCP port which results in missing or spotty data.

Hardware can be difficult to obtain and many of the terminal server designs have had no significant updates to the hardware or software. Many terminal servers in production today have a single 10BaseT Ethernet. The 10 MHz speed translates to 10 Mbit per second, which in theory means 1.2 Mbps. In practice though, the current terminal server is limited to no more than 800 kilobits per second (Kbps) because the 10BasetT Ethernet runs at half-duplex. Although that is sufficient bandwidth for serial devices running at 9600 bits per second, the half-duplex nature along with the limited processing power, makes these terminal servers susceptible to denial of service (intentional or unintentional), especially if network designs are not taking into consideration this risk.

However, terminal servers are very simple devices that require a signification amount of manual configuration, often using proprietary software or non-intuitive command line interfaces to configure, receive status updates, and reset serial port connections. Moreover, the TCP interface ports are not managed which can result in a loss of connectivity, which is not easily recognized until a clinician searches the EMR and realizes the data is missing. Even when it is determined that a loss of connectivity has occurred, clinicians are not equipped to troubleshoot the terminal server via proprietary software or command line utilities. Accordingly, support requests must be generated and routed through a support system until someone properly trained to troubleshoot the terminal server is available and on-site. This level of support results in numerous support requests for changes and simple management tasks which increases costs and time delays to support and manage the terminal servers.

Issues related to terminal servers have led to an implementation shift. In an effort to minimize network related impacts on the reliability of the terminal server, more hardware has been placed closer to the terminal server. For example, a CE appliance or a SOAD server are sometimes utilized to servers to connect the terminal servers to a bus that supports the healthcare information system. Although the additional hardware has helped to reduce some of the support related issues, the hardware costs have significantly increased.

Embodiments of the present disclosure relate to a multi-port communication device having a plurality of serial interfaces and a plurality of Transmission Control Protocol (TCP) interfaces. Data is received from one or more medical devices at a serial interface of the plurality of serial interfaces and communicated to a healthcare information system via a TCP interface of the plurality of TCP interfaces. The multi-port communication device can be remotely managed by a remote device via a set of management tools. In embodiments, the set of management tools run locally on the multi-port communication device. The multi-port communication device may additionally comprise locally installed drivers that enable communication with the healthcare information system via TCP.

In some embodiments, the multi-port communication device is a terminal server running management software (e.g., Connectivity Engine appliance software (CCE4)) which provides configuration and status access (at a port level) of the terminal server (including terminal server port resets). Further, the multi-port communication device is capable of running multiple containers (e.g., CCMHOST containers), which enables the device to be used beyond the laboratory.

In embodiments, the multi-port communication device is a hardware device with multiple serial interface ports (e.g., 8, 16 or 32). The device convert serial data from serially connected devices into a TCP data stream. This allows for communication with other systems across a network and allows data from the serially connected devices to be consumed by multiple other systems. Since both ends of the TCP connection are controlled in this model, automatic reconnection logic can be introduced which greatly service requests related to dropped connections.

In embodiments, other advantages of using the multi-port communication device include: remote management of the device, the ability to easily configure serial interface communication settings, the capability for external TCP connectivity to the serial interfaces, the ease of identifying the device and interacting with it, upgrading the device with new capabilities, ability to place software much closer to the serially connected devices on the network, automatic reconnection logic, and local hosting of driver software (and other software) provides greater flexibility in deployments (and enables the device to queue data until a connection is reestablished so no data is lost).

Accordingly, in one aspect, an embodiment is directed to one or more computer storage media having computer-usable instructions that, when used by one or more computing devices, cause the one or more computing device to perform operations. The operations include receiving data from one or more medical devices in a laboratory at a serial interface of a multi-port communication device. The multi-port communication device comprises a plurality of serial interfaces and a plurality of TCP interfaces. The operations also include communicating the data to a healthcare information system via a TCP interface of the plurality of TCP interfaces. The operations further include enabling remote management of the multi-port communication device by a remote device via a set of management tools. The set of management tools runs locally on the multi-port communication device.

In another aspect of the invention, an embodiment of the present invention is directed to a computer-implemented method in a clinical computing environment. The method comprises receiving data from one or more medical devices in a laboratory at a first serial interface of a multi-port communication device. The multi-port communication device comprises a plurality of serial interfaces and a plurality of TCP interfaces. The method also comprises receiving bedside data from one or more bedside monitor devices at a second serial interface of the multi-port communication device. The method further comprises receiving room control data from one or more room control devices at a third serial interface of the multi-port communication device. The method also comprises communicating the data to a healthcare information system via TCP interfaces of the plurality of TCP interfaces.

In a further aspect, an embodiment of the present invention is directed to a system. The system comprises one or more processors; and one or more computer storage media storing instructions that, when used by the one or more processors, cause the one or more processors to: receive data from one or more medical devices in a laboratory at a serial interface of a multi-port communication device, the multi-port communication device having a plurality of serial interfaces and a plurality of TCP interfaces; receive bedside data from one or more bedside monitor devices at a second serial interface of the multi-port communication device; receive room control data from one or more room control devices at a third serial interface of the multi-port communication device; communicate the data to a healthcare information system via TCP interfaces of the plurality of TCP interfaces; provide, via a user interface, a read only view of the multi-port communication device status to a display device in the laboratory; and enable remote management of the multi-port communication device by a remote device via user interface comprising a set of management tools, the set of management tools running locally on the multi-port communication device.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 104, provide storage of computer readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, students, office assistants and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 2:
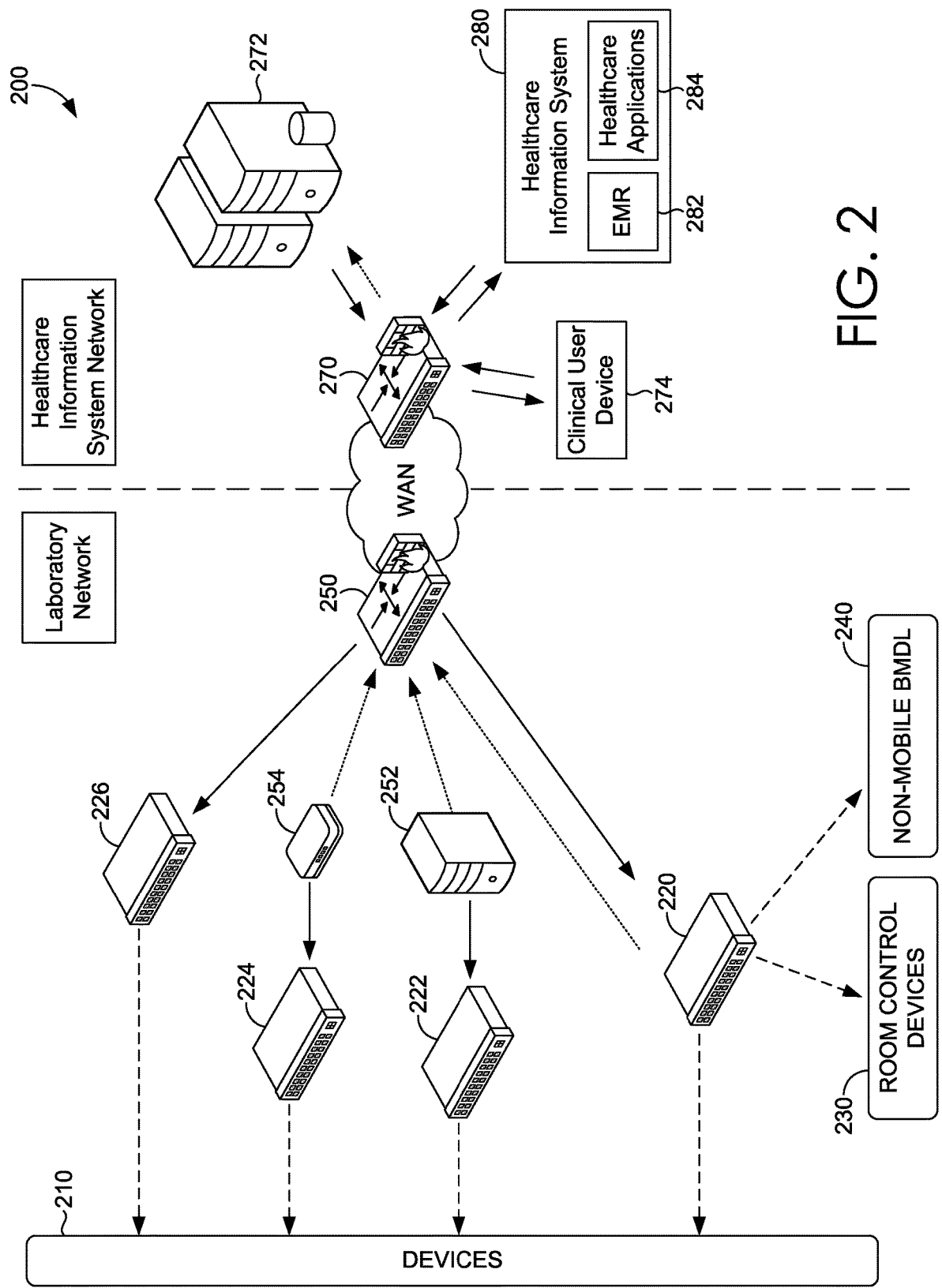
FIG. 2 is an exemplary system architecture suitable to implement embodiments of the present invention.

Turning now to FIG. 2, a schematic diagram depicts an operating environment, identified generally by reference numeral 200, suitable to practice an embodiment of the present invention. FIG. 2 includes various components that communicate with one another, including devices 210, terminal servers 220, 222, 224, 226, room control devices 230, non-mobile bedside monitor devices (BMD) 240, device gateway 250, SOAD server 252, CCE server 254, internal gateway 270, connectivity server 272, clinical user device 274, and healthcare information system 280. In one embodiment of the present invention, data generated by devices 210 or terminal server 270 is routed to and managed by clinical user device 274, as opposed to, devices 210 or terminal server 270 displaying information on the device or terminal server respectively. For example, data is communicated to connectivity server 272, which might then forward the data to device manager clinical user device 274 to be further processed and managed. Before describing in more detail how these components communicate, each component will be generally described.

In an embodiment of the present invention, devices 210 might include cardiac monitors, ventilators, balloon pumps, patient beds, sequential-compression devices, electronic security devices, infusion pumps, laboratory devices, and vital-sign detecting devices. Devices 210 may generate various data (e.g., measured heart rate) that, as described in more detail below, is communicated to other components (e.g., clinical user device 274 or EMR 282 via connectivity server 272) of operating environment 200. Moreover, devices 210 might also receive information from components of operating environment 200.

Healthcare information system 280 includes an integrated system of healthcare-related information that is usable by a healthcare facility to operate and provide patient care. For example, healthcare information system 280 includes an electronic medical record 282 (also referred to herein as "EMR") and a healthcare applications component 284. EMR 282 includes an electronic version of patient records including information for the patient, such as medication and infusion orders, tasks, images, examination reports, testing and lab results, medical history, etc. Healthcare applications component 284 includes information that is input and provided at a patient's point-of-care (e.g., patient bedside) to assist healthcare professionals to provide appropriate care. An exemplary applications component 284 includes a patient order entry component for entering electronic healthcare orders for a patient. In an embodiment of the present invention, healthcare information system 280 receives information from other components, as will be described in more detail below. Moreover, healthcare information system 280 might also provide information that is communicated to other components of operating environment 200.

Clinical user devices 274 include devices that are used within a healthcare facility to receive, display and send information to a user, such as a clinician. Clinical user devices 274 also facilitate requests to receive additional information. Exemplary clinical user devices 274 include personal clinical user devices and a clinician computer workstation. Personal clinical user devices include devices that are used by an individual to receive and send information, such as an in-house phone, a pager, and a mobile device. Workstations include a remote computer terminal that is used to present information to a user, such as a clinician, and receive input. Workstations might be set up at a nurse's station to or at a patient bedside. Accordingly, in an embodiment of the present invention, clinical user devices 274 present to users information that is received from other components of operating environment 200. Moreover, clinical user devices 274 might also receive inputs from a clinician that are communicated to other components of operating environment 200. Clinical user devices 274 also communicate to other components of operating environment 200 requests to receive additional information. For example, clinical user device might communicate to or receive information from terminal server 220 (e.g., configuration information or alerts).

As previously indicated, and as depicted in FIG. 2, each of devices 210, terminal servers 220, 222, 224, 226, SOAD server 252, CCE server 254, clinical user device 274, and healthcare information system 280, may be in communication with connectivity server 272. Connectivity server 272 (e.g., CareAware® iBus) generally provides a connection framework for these components by creating and managing all connections, providing a messaging architecture to facilitate an exchange of information between the various components of FIG. 2, and providing general operational and management capabilities for connected devices. In one embodiment, each of devices 210, terminal servers 220, 222, 224, 226, SOAD server 252, CCE server 254, clinical user device 274, and healthcare information system 280 communicate with connectivity server 272 as described in U.S. patent application Ser. No. 12/347,475 (U.S. patent application '475), which is incorporated herein by reference. As such, components of FIG. 2 might communicate with connectivity server 272 via a gateway (e.g., device gateway 250 or internal gateway 270), an adapter, or by any other means described by U.S. patent application '475. In a further embodiment, connectivity server 272 includes those capabilities described in U.S. patent application '475 (e.g., capabilities of main bus). As indicated in U.S. patent application '475, once data is received it can be sorted and routed to other applications.

As such, connectivity server 272 might receive information from terminal server 220 (e.g., data from devices 210 or port information from terminal server 220) and route the data to EMR 280 or clinical user device 274. Moreover, connectivity server 272 might receive information (e.g., configuration information) from clinical user device 274 and route the information to terminal server 220. In a further embodiment, connectivity server 272 receives information from healthcare information system 228 and routes the information to terminal server 220.

In an embodiment of the present invention, terminal server 220 communicates with connectivity server 272, which functions to consolidate and manage information received from the various components of operating environment 200. The terminal server 220 includes locally installed drivers that enable communication with the healthcare information system via TCP. The locally installed drivers enable external TCP connectivity (e.g., the connectivity server 272) to the plurality of serial interfaces, which enables communication and configuration without additional hardware. In this embodiment, instead of requiring additional hardware at the terminal server 222, 224, and 226 (e.g., SOAD server 252, CCE server 254) information is routed through and processed by terminal server 220. For example, terminal server 220 manages and launches drivers for via a gateway (e.g., device gateway 250 or internal gateway 270) to facilitate communication with external devices (e.g., connectivity server 272).

Additionally or alternatively, terminal server 220 hosts software components corresponding to the health information system. This enables data to be communicated to the healthcare information system utilizing Java Message Service (which provides much greater security for the data being communicated than typical TCP communication). For example, terminal server 220 enables the information to be communicated externally to the connectivity server 272 via Java Message Service (JMS), rather than via TCP (which is not secure).

In embodiments, a set of management tools installed locally on the terminal server 220 may provide an indication that a particular device is connected to terminal server 220 and/or communicating with connectivity server 272. Based on this data, a user may configure or manage the connection of the particular device via the set of management tools accessed by clinical user device 274 or a display device connected to the terminal server 220 itself. In other words, remote management of the terminal server 220 is enabled by a remote device (e.g., clinical user device 274) via a user interface provided by the set of management tools. For clarity, the set of management tools runs locally on the terminal server 220.

Additionally, or alternatively, if the particular device has lost a connection to the connectivity server 272, the set of management tools may automatically reestablish the connection. The terminal server 220 queues any data received by the particular device until the connection has been reestablished. At that point, the terminal server 220 pushes the queued data to the connectivity server 272.

In practice, data is received from one or more medical devices (e.g., devices 210) in a laboratory at a serial interface of a multi-port communication device, such as terminal server 220. The multi-port communication device comprises a plurality of serial interfaces and a plurality of TCP interfaces. In embodiments, bedside data is received from one or more bedside monitor devices 240 at a second serial interface of the multi-port communication device. Additionally or alternatively, room control data is received from one or more room control devices 230 at a third serial interface of the multi-port communication device.

The data, the bedside data, and the room control data is communicated to a healthcare information system 280 via TCP interfaces of the plurality of Transmission Control TCP interfaces. To do so, the terminal server 220 may communicate data to the connectivity server 272 via a device gateway 250 (externally) across the internet to an internal gateway 270 (internally).

Additionally, a read only view of the terminal server 220 status is provided, via a user interface, to a display device in the laboratory. This enables a clinician to determine whether the terminal server 220 is properly configured at the time the device is performing, rather than waiting until the clinician later determines data is missing from the EMR 282. In embodiments, the multi-port communication device hosts software components corresponding to the health information system 280. This prevents data loss because if a connection drops, the device queues data until the connection is reestablished. In addition, because connectivity back to the connectivity server 272 is internal (e.g., JMS), any information communicated by the device or any software components hosted thereon is done so securely.

Figure 3:
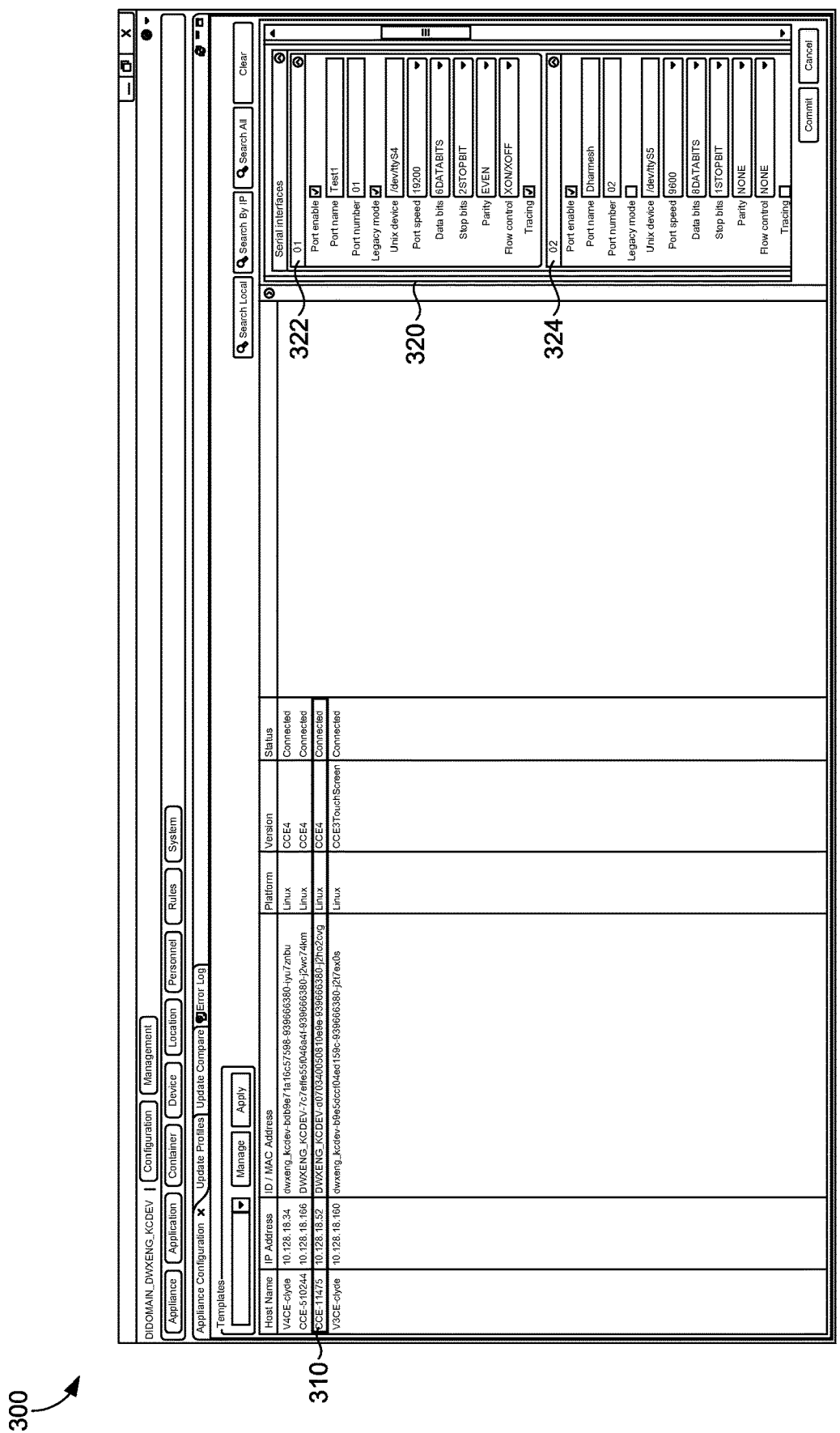
FIGS. 3-5 are screenshots of graphical user interfaces in accordance with embodiments of the present invention.

Turning now to FIG. 3, an illustrative graphical user interface 300 is shown for a management view of the serial interfaces for the terminal server, in accordance with an embodiment of the present invention. As illustrated, a list of terminal servers is displayed (e.g., terminal server 310). A user can select a particular terminal server to see the serial interfaces 320 associated with that terminal server. From this perspective, the user can configure or manage individual ports 322, 324 of the terminal server.

Figure 4:
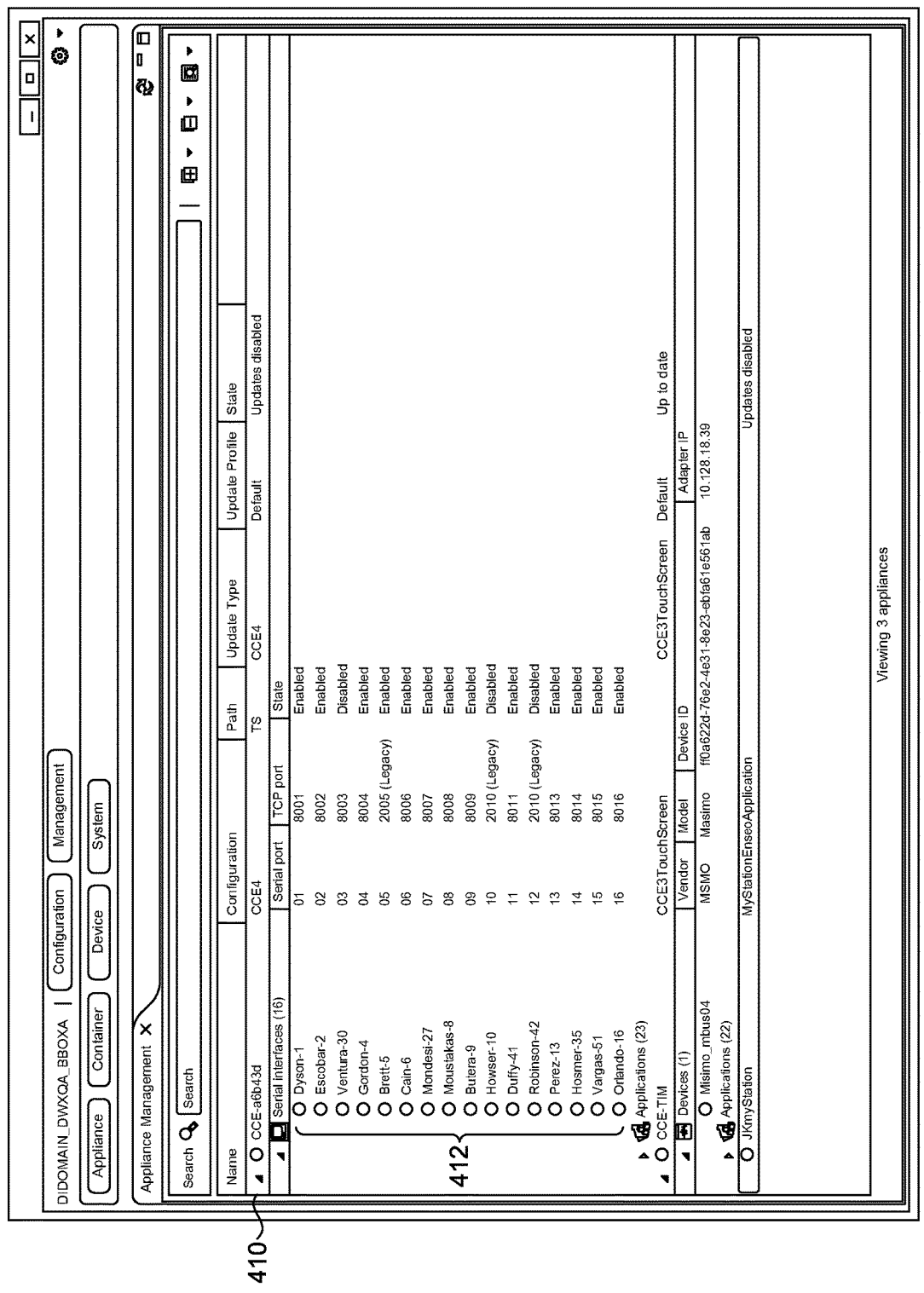

Turning now to FIG. 4, an illustrative graphical user interface 400 is shown for a management view of the serial interfaces for the terminal server, in accordance with an embodiment of the present invention. As illustrated, a list of terminal servers is displayed (e.g., terminal server 410). A user can expand a particular terminal server to see the serial interfaces 412 associated with that terminal server. From this perspective, the user can reset individual ports of the terminal server.

Figure 5:
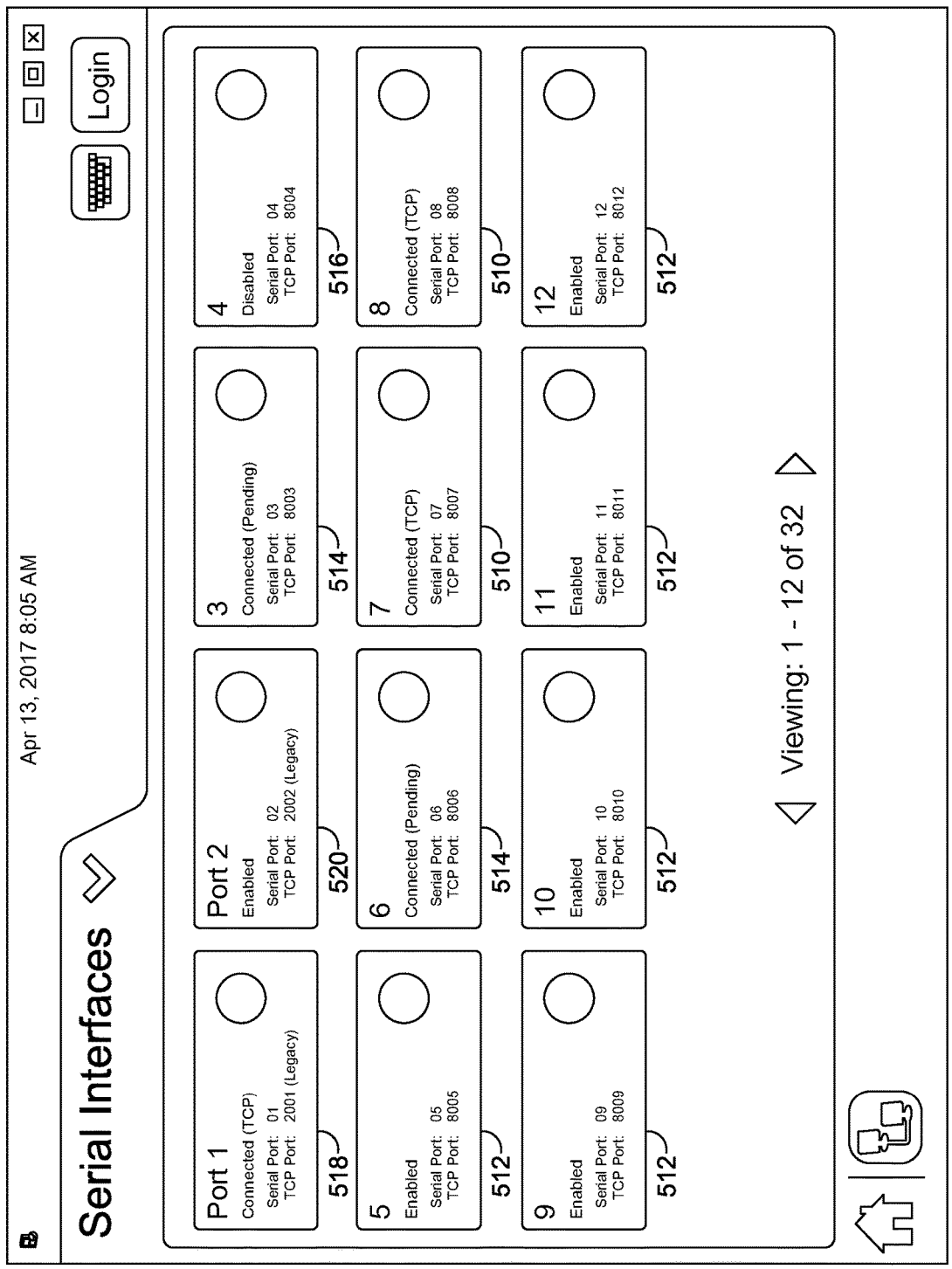

Turning now to FIG. 5, an illustrative graphical user interface 500 is shown indicating a status of the serial interfaces for the terminal server (which can be displayed either via a direct connection (e.g., a VGA interface) to the terminal server with a display device or remotely, as described herein), in accordance with an embodiment of the present invention. As illustrated, the serial ports 510 are connected via TCP. Each of the serial ports 510 indicates the status (connected (TCP)), the serial port number, and the TCP port number. Serial ports 512 are enabled ports. Like serial ports 510, each of the serial ports 512 indicates the status (enabled), the serial port number, and the TCP port number.

Serial ports 514 have connections pending. Each of serial ports 514 indicate the status (pending), the serial port number, and the TCP port number. Serial port 516 is a disabled port. Serial port 516 indicates the status (disabled), the serial port number, and the TCP port number. Serial port 518 is connected via TCP. Serial port indicates the status (connected (TCP)), the serial port number, and the TCP port number. The difference between serial port 518 and serial ports 510 is that serial port 518 has a legacy TCP port number (as indicated by the TCP port number). This indicates the data communicated from the device connected to this port does not use JMS to communicate securely with the connectivity server. Rather, these ports utilize raw TCP sockets. Similarly, serial port 520 indicates the port is enabled with a legacy TCP port number. As with the other serial ports, serial port 520 also indicates the status (enabled), the serial port number, and the TCP port number.

Figure 6:
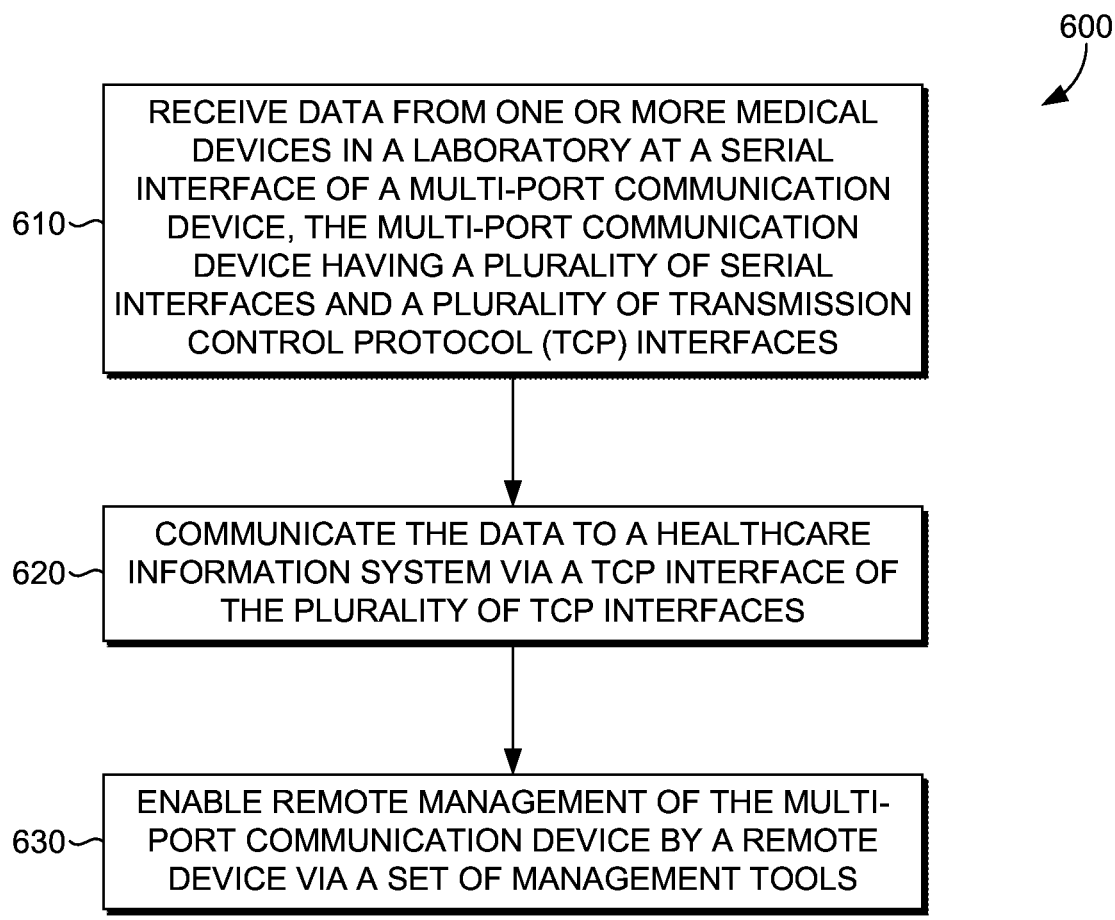
FIG. 6 is a flow diagram showing a method for utilizing and managing a multi-port communication device, in accordance with embodiments of the present invention.

Turning now to FIG. 6, a flow diagram is provided that illustrates a method 600 for utilizing a serial interface to transmission control protocol interface multi-port communication device, in accordance with embodiments of the present invention. At step 610, data is received from one or more medical devices in a laboratory at a serial interface of a multi-port communication device. The multi-port communication device comprises a plurality of serial interfaces and a plurality of Transmission Control Protocol (TCP) interfaces.

In some embodiments, bedside data is received from one or more bedside monitor devices at a second serial interface of the multi-port communication device. The bedside data is communicated to the healthcare information system via a second TCP interface of the plurality of TCP interfaces.

Additionally or alternatively, room control data may be received from one or more room control devices at a third serial interface of the multi-port communication device. The room control data is communicated to the healthcare information system via a third TCP interface of the plurality of TCP interfaces.

At step 620, the data is communicated to a healthcare information system via a TCP interface of the plurality of TCP interfaces. In embodiments, the multi-port communication device comprises locally installed drivers that enable communication with the healthcare information system via TCP. The locally installed drivers enable external TCP connectivity to the plurality of serial interfaces, which enables communication without additional hardware.

Additionally or alternatively, the multi-port communication device hosts software components corresponding to the health information system. This enables data to be communicated to the healthcare information system externally utilizing JMS (which provides much greater security for the data being communicated because it is encrypted, rather than typical unencrypted TCP communication).

At step 630, remote management of the multi-port communication device by a remote device is enabled via a set of management tools. The set of management tools runs locally on the multi-port communication device. Importantly, the set of management tools enable configuration of serial interface communication settings of the multi-port communication device (such as from an external device, for example, the clinical user device 274 of FIG. 2). In some embodiments, the set of management tools detects connection issues between the serial interfaces and the TCP interfaces. Automatic reconnection between the serial interface and the TCP interface may further be enabled by the set of management tools. In embodiments, a read only view of the multi-port communication device status is provided to a display device in the laboratory.

Figure 7:
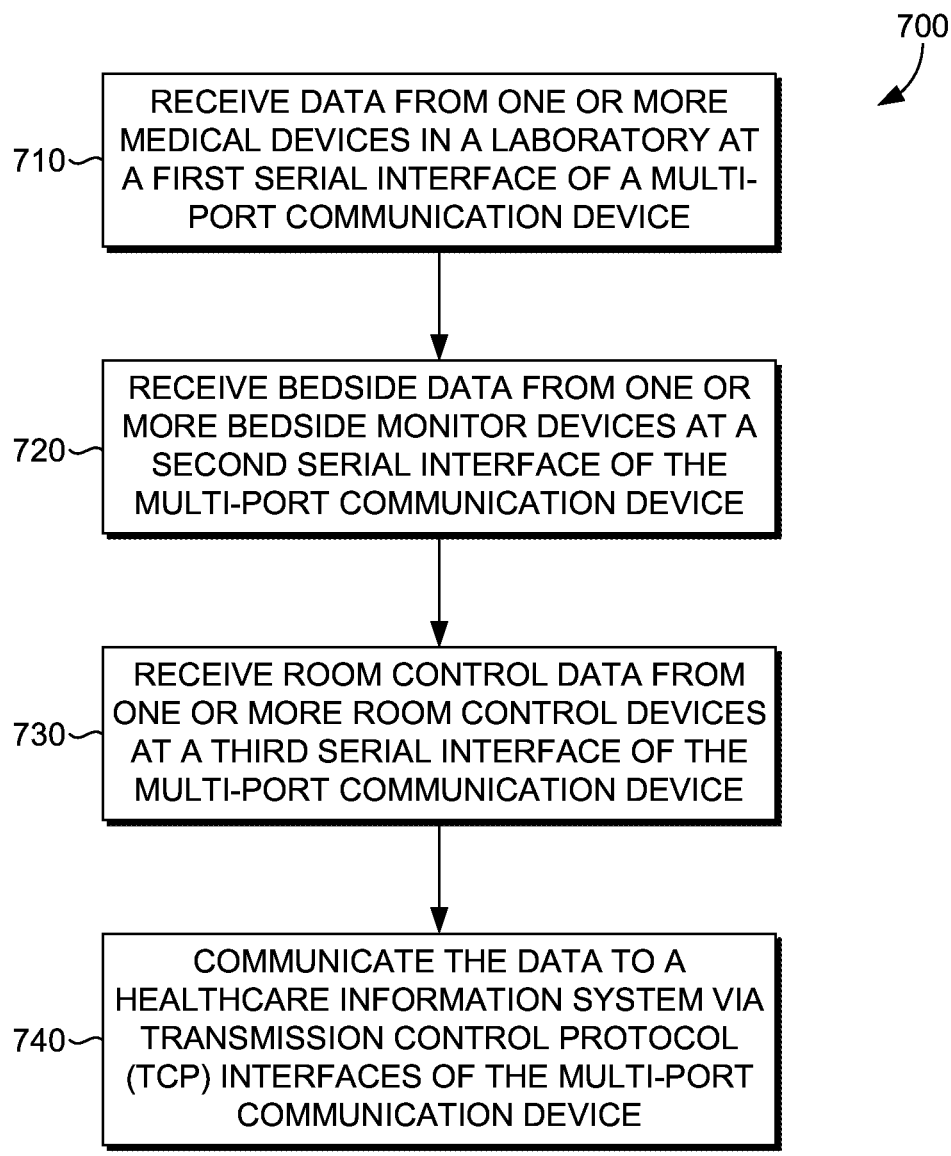
FIG. 7 is a flow diagram showing a method for communicating data to a healthcare information system via a multi-port communication device, in accordance with embodiments of the present invention.

With reference now to FIG. 7 a flow diagram is provided that illustrates a method 700 for utilizing a serial interface to transmission control protocol interface multi-port communication device, in accordance with embodiments of the present invention. At block 710, data is received from one or more medical devices (e.g., devices 210 of FIG. 2) in a laboratory at a first serial interface of a multi-port communication device (e.g., terminal server 220 of FIG. 2). The multi-port communication device comprises a plurality of serial interfaces and a plurality of TCP interfaces.

Bedside data is received, at step 720, from one or more bedside monitor devices at a second serial interface of the multi-port communication device. At step 730, room control data is received from one or more room control devices (e.g., room control devices at a third serial interface of the multi-port communication device. The data is communicated, at step 740, to a healthcare information system via TCP interfaces of the plurality of TCP interfaces.

In some embodiments, a read only view of the multi-port communication device status is provided to a display device in the laboratory. Remote management of the multi-port communication device by a remote device may be enabled via a set of management tools. The set of management tools runs locally on the multi-port communication device. The set of management tools enables configuration of serial interface communication settings of the multi-port communication device.

In some embodiments, the multi-port communication device comprises locally installed drivers that enable communication with the healthcare information system via TCP. The locally installed drivers enable external TCP connectivity to the plurality of serial interfaces. The multi-port communication device may host software components corresponding to the health information system.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

What is claimed is:

1. One or more computer storage media storing computer-useable instructions that, when used by one or more computing devices, cause the one or more computing devices to perform operations comprising:

receiving data from one or more medical devices in a laboratory at a serial interface of a multi-port communication device, the multi-port communication device comprising a plurality of serial interfaces a plurality of Transmission Control Protocol (TCP) interfaces, and software components corresponding to a healthcare information system;

communicating the data to the healthcare information system via a TCP interface of the plurality of TCP interfaces; and enabling remote management of the multi-port communication device by a remote device via a set of management tools, wherein the set of management tools:
runs locally on the multi-port communication device;
enables configuration of serial interface communication settings of the multi-port communication device; and
upon the multi-port communication device losing a connection with a connectivity server, utilizing the software components to automatically queue any data the particular device receives from the one or more medical devices until the connection with the connectivity server is reestablished.

2. The media of claim 1, further comprising providing a read only view of the multi-port communication device status to a display device in the laboratory.

3. The media of claim 1, wherein the multi-port communication device comprises locally installed drivers that enable communication with the healthcare information system via TCP.

4. The media of claim 3, wherein the locally installed drivers enable external TCP connectivity to the plurality of serial interfaces.

5. The media of claim 1, further comprising receiving bedside data from one or more bedside monitor devices at a second serial interface of the multi-port communication device.

6. The media of claim 5, further comprising communicating the bedside data to the healthcare information system via a second TCP interface of the plurality of TCP interfaces.

7. The media of claim 1, further comprising receiving room control data from one or more room control devices at a third serial interface of the multi-port communication device.

8. The media of claim 7, further comprising communicating the room control data to the healthcare information system via a third TCP interface of the plurality of TCP interfaces.

9. The media of claim 1, wherein the set of management tools is accessed by a clinical user device in communication with the multi-port communication device.

10. The media of claim 1, wherein the software components enable the data to be communicated to the healthcare information system utilizing Java Message Service.

11. The media of claim 10, wherein the data is communicated by the multi-port communication device to the healthcare information system without requiring additional hardware to connect the multi-port communication device to a bus that supports the healthcare information system.

12. The media of claim 1, wherein the set of management tools additionally provides an indication that the particular device of the one or more medical devices is connected to the multi-port communication device or communicating with the connectivity server.

13. A computer-implemented method in a clinical computing environment comprising:
receiving data from one or more medical devices in a laboratory at a first serial interface of a multi-port communication device, the multi-port communication device comprising a plurality of serial interfaces, a plurality of Transmission Control Protocol (TCP) interfaces, and software components corresponding to a healthcare information system;
receiving bedside data from one or more bedside monitor devices at a second serial interface of the multi-port communication device;
receiving room control data from one or more room control devices at a third serial interface of the multi-port communication device;
communicating data comprising the besides data and the room control data to the healthcare information system via TCP interfaces of the plurality of TCP interfaces;
providing a read only view of the multi-port communication device status to a display device in the laboratory; and
enabling remote management of the multi-port communication device by a remote device via a set of management tools, wherein the set of management tools:
runs locally on the multi-port communication device;
enables configuration of serial interface communication settings of the multi-port communication device; and
upon the multi-port communication device losing a connection with a connectivity server, utilizing the software components to automatically queue any data the particular device receives from the one or more medical devices until the connection with the connectivity server is reestablished.

14. The method of claim 13, wherein the multi-port communication device comprises locally installed drivers that enable communication with the healthcare information system via Java Message Service.

15. The method of claim 13, wherein the software components enable the data to be communicated to the healthcare information system utilizing Java Message Service, and wherein the data is communicated by the multi-port communication device to the healthcare information system without requiring additional hardware to connect the multi-port communication device to a bus that supports the healthcare information system.

16. The method of claim 13, wherein the multi-port communication device comprises locally installed drivers that:
enable communication with the healthcare information system via TCP; and
enable external TCP connectivity to the plurality of serial interfaces, which enables communication and configuration without additional hardware.

17. A system comprising:
one or more processors; and
one or more computer storage media storing instructions that, when used by the one or more processors, cause the one or more processors to:
receive data from one or more medical devices in a laboratory at a serial interface of a multi-port communication device, the multi-port communication device comprising a plurality of serial interfaces a plurality of Transmission Control Protocol (TCP) interfaces, and software components corresponding to a healthcare information system;
receive bedside data from one or more bedside monitor devices at a second serial interface of the multi-port communication device;
receive room control data from one or more room control devices at a third serial interface of the multi-port communication device;
communicate the data, the bedside data, and the room control data to the healthcare information system via Transmission Control Protocol (TCP) interfaces of the plurality of TCP interfaces;
provide, via a user interface, a read only view of the multi-port communication device status to a display device in the laboratory; and
enable remote management of the multi-port communication device by a remote device via a user interface comprising a set of management tools, wherein the set of management tools:
runs locally on the multi-port communication device;
enables configuration of serial interface communication settings of the multi-port communication device; and
upon the multi-port communication device losing a connection with a connectivity server, utilizing the software components to automatically queue any data the particular device receives from the one or more medical devices until the connection with the connectivity server is reestablished.

18. The system of claim 17, wherein the set of management tools additionally provides an indication that the particular device of the one or more medical devices is connected to the multi-port communication device or communicating with the connectivity server.

19. The system of claim 17, wherein the software components enable the data to be communicated to the healthcare information system utilizing Java Message Service, and wherein the data is communicated by the multi-port communication device to the healthcare information system without requiring additional hardware to connect the multi-port communication device to a bus that supports the healthcare information system.

\* \* \* \* \*

UNITED STATES PATENT AND TRADEMARK OFFICE
CERTIFICATE OF CORRECTION

PATENT NO. : 10,630,814 B2
APPLICATION NO. : 15/689732
DATED : April 21, 2020
INVENTOR(S) : Michael Thomas Barnes et al.

Page 1 of 1

It is certified that error appears in the above-identified patent and that said Letters Patent is hereby corrected as shown below:

In the Claims

Column 12, Line 48 Claim 1: Please remove "interfaces" and replace with --interfaces,--.

Column 14, Line 39 Claim 17: Please remove "interfaces" and replace with --interfaces,--.

Signed and Sealed this
Sixteenth Day of June, 2020

Andrei Iancu
*Director of the United States Patent and Trademark Office*